(12) United States Patent
Pinset

(10) Patent No.: US 8,759,022 B2
(45) Date of Patent: Jun. 24, 2014

(54) METHOD FOR SELECTING MEVALONATE SYNTHESIS MODULATORS USING CELLS DERIVED FROM HUMAN PLURIPOTENT CELLS

(75) Inventor: Christian Pinset, Paris (FR)

(73) Assignee: Centre d'Etude des Cellules Souches, Evry (FR)

( * ) Notice: Subject to any disclaimer, the term of this patent is extended or adjusted under 35 U.S.C. 154(b) by 0 days.

(21) Appl. No.: 13/805,547

(22) PCT Filed: Jun. 20, 2011

(86) PCT No.: PCT/IB2011/052680
§ 371 (c)(1),
(2), (4) Date: Feb. 5, 2013

(87) PCT Pub. No.: WO2011/161611
PCT Pub. Date: Dec. 29, 2011

(65) Prior Publication Data
US 2013/0210059 A1   Aug. 15, 2013

(30) Foreign Application Priority Data
Jun. 21, 2010   (EP) ................. 10166631

(51) Int. Cl.
*C12Q 1/02* (2006.01)
(52) U.S. Cl.
USPC ........................................... 435/29
(58) Field of Classification Search
USPC .................................... 435/29, 30
See application file for complete search history.

(56) References Cited

U.S. PATENT DOCUMENTS

| 2006/0258003 | A1 | 11/2006 | Pinset |
| 2009/0081784 | A1 | 3/2009 | Vodyanyk et al. |
| 2010/0166713 | A1* | 7/2010 | Dalton et al. ............... 424/93.7 |
| 2010/0267135 | A1* | 10/2010 | Sakurada et al. ........... 435/366 |

FOREIGN PATENT DOCUMENTS

| WO | WO-2004/055174 | 7/2004 |
| WO | WO-2005/111197 | 11/2005 |
| WO | WO-2008/094597 | 8/2008 |
| WO | WO-2008/150498 | 12/2008 |

OTHER PUBLICATIONS

McNeish John. Embryonic Stem Cells in Drug Discovery. Nature Reviews Drug Discovery 3:70-80, Jan. 2004.*
Takamizawa S. et al. Effects of Ascorbic Acid and Ascorbic Acid 2-Phosphate . . . Cell Biology International 28(4)255-265, 2004.*
Boyd, N. L., et al.; "Human Embryonic Stem Cell-Derived Mesoderm-like Epithelium Transitions to Mesenchymal Progenitor Cells;" Tissue Engineering Part A; vol. 15, No. 8; dated Jan. 15, 2009.
De Peppo, G. M., et al.; "Human Embryonic Mesodermal Progenitors Highly Resemble Human Mesenchymal Stem Cells and Display High Potential for Tissue Engineering Applications;" Tissue Engineering Part A; vol. 16, No. 7; dated Mar. 10, 2010.
International Search Report for Application No. PCT/IB2011/052680; dated Dec. 1, 2011.
Karlsson, C., et al.; "Human embryonic stem cell-derived mesenchymal progenitors—Potential in regenerative medicine;" Stem Cell Research; vol. 3, No. 1; dated May 7, 2009.
Kitagawa, M., et al.; "Differentiation of mesodermal cells from pluripotent stem cells;" International Journal of Hematology; vol. 91, No. 3; dated Mar. 12, 2010.

* cited by examiner

*Primary Examiner* — Ralph Gitomer
(74) *Attorney, Agent, or Firm* — Alston & Bird LLP

(57) ABSTRACT

The invention provides a method for selecting pharmaceutical compounds affecting mevalonate or cholesterol. The method having a step for putting into contact with the pharmaceutical compounds to be tested, cells of the MSC type obtained by a method for producing cells of the MSC type from human pluripotent cells or from induced stem cells, including a step for cultivating human pluripotent cells or induced stem cells in a culture medium of: 1) one or more growth factors selected from FGFs, HGF, PDGFs, EGF, herugulins and VEGFs; and 2) one or more antioxidants selected from ascorbic acid and its derivatives, vitamin E and N-acetylcysteine.

4 Claims, No Drawings

METHOD FOR SELECTING MEVALONATE SYNTHESIS MODULATORS USING CELLS DERIVED FROM HUMAN PLURIPOTENT CELLS

This application is a National Stage application filed under Rule 371 based upon PCT/IB11/52680 filed May 20, 2011.

FIELD OF THE INVENTION

The synthesis of mevalonate is involved in many biological processes such as the synthesis of cholesterol, as well as the prenylation of proteins. The different steps of the metabolic route have been identified. The limiting HMG CoA reductase, an enzyme for the synthesis of mevalonate, is a major therapeutic target. Statins which are competitive inhibitors of HMG CoA reductase form an important class of therapeutic molecules. The first clinical application of these molecules is the reduction of lipoproteins of the LDL types in the general blood stream. Moreover, these molecules have pleiotropic effects, some of which are independent of the control of the synthesis of cholesterol and probably related to secondary modifications of the proteins involved in cell signaling. Statins improve the function of endothelial cells, stabilize atheroma plates, have anti-inflammatory functions, play a role in bone resorption, reduce the risks of dementia, control cell proliferation of certain normal and tumoral cells.

Moreover, statins have significant toxicity for certain tissues such as muscle tissue, which limits the clinical use thereof.

Cell tests allowing high throughput screening of compounds interfering with the metabolism of mevalonate should allow:

Identification of novel functional inhibitors of the synthesis of mevalonate.
Providing drug interactions having the consequences of increasing cell toxicity, in particular muscular toxicity.
Identification of molecules preventing tissue toxicity, in particular muscular toxicity.
Identification of molecules preventing muscle atrophy.
Identification of molecules selectively controlling the proliferation of normal and tumoral cells, including tumoral stem cells.

The present invention relates to methods for screening molecules involved in the synthesis of mevalonate notably by using differentiated normal MSC cells or of the MSC type, derived from pluripotent cells.

SUMMARY OF THE INVENTION

The efficiency of high throughput screening by using cell tests, is dependent on the specificity, on the sensitivity, on the robustness and availability of the cell tests used. This issue is particularly important for normal human cells which are the most suitable models for screening therapeutic molecules for the human species. Indeed, the availability of normal human cells is in particular limited for certain cell types such as cardiac and neural cells. On the other hand, normal human cells have limited replication capacity restricting their use for high throughput screening. Presently, the large majority of the cells used for high throughput screenings of the HTS type are either non-human cells or else transformed or tumoral human cells which decreases the relevance of the isolated molecules in this type of screening.

The present invention relates to methods for high throughput screening of molecules involved in the synthesis of mevalonate by using differentiated normal MSC cells or of the MSC type derived from pluripotent cells. The invention also relates to methods for producing differentiated normal cells derived from pluripotent cells. The invention also relates to methods for high throughput screening using differentiated normal cells derived from pluripotent cells by controlling the synthesis of mevalonate by the presence of pharmacological inhibitors.

The object of the present invention is notably:

1. A method for producing cells of the MSC type from human pluripotent cells comprising a step for cultivating human pluripotent cells in a culture medium comprising:
   a. one or several growth factors selected from FGFs, HGFs, PDGFs, EGF, herugulins and VEGFs
   b. one or more antioxidants selected from ascorbic acid and its derivatives, vitamin E and N-acetylcysteine
2. A method for producing cells of the MSC type from induced pluripotent stem cells comprising a step for cultivating the induced stem cells in a culture medium comprising:
   a. one or more growth factors selected from FGFs, HGF, PDGFs, EGF, herugulins and VEGFs
   b. one or more antioxidants selected from ascorbic acid and its derivatives, vitamin E and N-acetylcysteine.
3. The method according to object 1 or 2 characterized in that the culture medium comprises:
   a. FGF; and
   b. ascorbic acid or one of its derivatives.
4. The method according to object 3 characterized in that the culture medium comprises:
   a. FGF2; and
   b. ascorbic acid and/or ascorbic acid 2-phosphate.
5. The method according to object 4 characterized in that the culture medium comprises FGF2 at a final concentration of 10 ng/mL and ascorbic acid 2-phosphate at a final concentration of 1 mM.
6. The method according to the preceding objects, characterized in that the produced cells of the MSC type express one or more of the CD73, CD29, CD44, CD 166 or CD 105 markers.
7. The method according to the preceding objects characterized in that the produced cells of the MSC type express SSEA4.
8. A method for selecting pharmaceutical compounds affecting mevalonate or cholesterol, comprising a step for putting the cells obtained by the methods of objects 1 to 7 into contact with the pharmaceutical compounds to be tested.
9. A method for selecting pharmaceutical compounds modulating the metabolic routes of mevalonate or cholesterol, comprising a step for putting the cells obtained by the methods of objects 1 to 7 into contact with the pharmaceutical compounds to be tested.
10. A method for selecting pharmaceutical compounds enhancing the effects of inhibition of the synthesis of mevalonate, comprising a step for putting the cells obtained by the methods of objects 1 to 7 into contact with the pharmaceutical compounds to be tested.
11. A method for selecting pharmaceutical compounds compensating for the effects of the inhibition of the synthesis of mevalonate, comprising a step for putting the cells obtained by the methods of objects 1 to 7 into contact with the pharmaceutical compounds to be tested.
12. A method for selecting pharmaceutical compounds, functional inhibitors of the synthesis of mevalonate and of cholesterol, comprising a step for putting the cells obtained by the methods of objects 1 to 7 into contact with the pharmaceutical compounds to be tested.
13. A method for selecting pharmaceutical compounds having a toxic effect on muscular tissue, comprising a step for putting the cells obtained by the methods of objects 1 to 7 into contact with the pharmaceutical compounds to be tested.
14. A method for selecting pharmaceutical compounds protecting against muscle atrophy or sarcopenia, comprising a step for putting the cells obtained by the methods of objects 1 to 7 into contact with the pharmaceutical compounds to be tested.
15. A method for selecting antitumoral pharmaceutical compounds comprising a step for putting the cells obtained by the methods of objects 1 to 7 into contact with the pharmaceutical compounds to be tested.
16. Cells obtained by the methods of objects 1 to 7 for repairing bone tissue.
17. Cells obtained by the methods of objects 1 to 7 for repairing cartilage.
18. The use of cells obtained by the methods of objects 1 to 7 for obtaining white or brown adipocytes.
19. The use of cells obtained by the methods of objects 1 to 7 for obtaining immunomodulating cells.

DESCRIPTION OF THE INVENTION

The present invention relates to methods for high input screening of molecules involved in the synthesis of mevalonate by using differentiated normal MSC cells or of the MSC type derived from pluripotent cells. One of the goals of this novel method is to increase robustness, specificity and sensitivity of the high throughput screenings by associating sources of normal human cells available in an unlimited amount and modulators of the synthesis of mevalonate. The specificity, sensitivity, robustness and availability of cell systems determine the relevance of high throughput screenings.

Very frequently, the cells used for high throughput screenings are cells of rodents (rat, mouse) or transformed human cells. Unlike many rodent cells which have significant probabilities of spontaneous transformation, normal human cells have finite growth capacities and enter senescence after about 50 cell divisions. The extended growth of human cells is accompanied by phenotype instability. These properties considerably limit the use of normal human cells for high throughput screenings.

The existence of human pluripotent stem cells gives the possibility of having access to normal human cells without any limitations. There exist two types of pluripotent cells: embryonic stem cells (hES) and induced stem cells (iPS). The essential characteristics of pluripotent cells are the capability of self-renewal without any limitation and the possibility of differentiation into all the types of cells making up an entire organism.

The possibility since the work of J. Thompson (Thompson et al. 1998) of using human embryonic stem cells (hES) has opened a large number of possibilities.

Experimentally, human embryonic stem cells have allowed development of differentiation procedures and isolation of many types of cells (cardiac cells, smooth muscle cells, neural cells, keratinocytes, hematopoietic cells, insulin-producing cells). However, the isolation of embryonic stem cells is a technology which requires significant know-how and which is dependent on accessing sensitive and limited biological material: supernumerary embryos. Further, embryonic stem cells raise many ethical issues which are solved differently depending on the national states. Ethical, regulatory and industrial property issues presently limit the use of embryonic stem cells.

The discovery of iPS cells by the team led by S. Yamanaka (Takahashi K. & Yamanaka S. 2006) has shown the reversible nature of the latter and the reduced number of genes for which <<forced>> co-expression may cause dedifferentiation and reprogramming of cells of very diverse types into iPS cells having properties very similar to ES cells: self-renewal, differentiation capability into all cell types making up an organism and capability of forming teratomas once ejected into tolerant animals. There does not seem to exist any limitations for obtaining iPS. Indeed, primary cells, immortalized cells, skin or lung fibroblasts, hepatocytes, pancreas cells, lymphocytes and neural precursors were able to be <<reprogrammed>> into iPS cells. iPS cells stemming from cells of patients affected with many pathologies such as SMA, ALS, Parkinson's or Duchenne's Dystrophy have also been produced (Park et al. Et 2008). This approach therefore allows isolation of iPS cells from easily accessible biological materials. Finally, it must be added that these very numerous studies clearly show the qualitative robustness of this technology.

The first part of the invention relates to the production of differentiated MSC cells or of the MSC type derived from pluripotent cells sensitive to the inhibitors of HMG CoA reductase, a key enzyme in the synthesis of mevalonate. Former studies have shown that cells derived from muscular tissue, muscle precursor cells (MPC), have particular sensitivity to statins. Indeed, the presence of statin specifically inhibits the growth of this type of cells. The described method of the invention allows production of differentiated cells sensitive to inhibitors of HMG CoA reductase derived from pluripotent cells: hES cells and iPS cells. The production method is a two-step method, the first step being a differentiation method from pluripotent cells and the second being a method for amplifying and preserving thereby differentiated cells.

The different steps of the production method are described below. The principle of this method is to initiate differentiation by mechanical or enzymatic disassociation of non-differentiated cell clusters stemming from pluripotent cells and by sowing on a cell support consisting of collagen or of its derivatives such as gelatin. Once the cells are differentiated, the cells are amplified in a medium comprising growth factors from the FGF family and antioxidants such as the derivatives of ascorbic acid. For this purpose, other growth factors may be used such as HGF (Hepatocyte Growth Factor), various PDGFs (Platelet Derived Growth Factor), factors from the EGF (Epidermal Growth Factor) family, from the VGEF family, herugulins. With this method, it is possible to produce differentiated cells without any limitations on amounts, which have a stable phenotype. These cells have a normal phenotype which is characterized by a normal karyotype and by finite growth.

DEFINITIONS OF THE CELL TYPES

Pluripotent Stem Cells

Pluripotent cells are characterized by two properties: the self-renewal capability and that of forming all the cell types making up an adult organism. These cells by differentiation may give cells of the free embryonic layers (ectodermis, endodermis, mesodermis). There essentially exist two types of pluripotent cells, embryonic stem cells and cells induced to pluripotency.

Embryonic Stem Cells (ES Cells).

Embryonic stem cells are pluripotent stem cells stemming from an embryo in the blastocyst stage. Isolation of these cells required resorting to embryos. Today, there exist worldwide very numerous lines of embryonic stem cells which are available.

Induced Pluripotent Stem Cells (iPS Cells)

Induced pluripotent stem cells (iPS) stem from reprogramming adult somatic cells into pluripotent cells, are, for the moment in the large majority of the cases, obtained by transfer of genes required for reprogramming. Among these genes, genes expressed by ES cells are found such as Sox2 and Oct4 and genes controlling proliferation such as cMyc, Lin 28 and Klf4. iPS cells have the essential properties of ES cells. In the near future, it will be possible to obtain iPSes by using other approaches such as transfer of proteins, treatment with small molecules.

Mesodermal Progenitor Cells (MePC)

<<MSC>> cells are derived from pluripotent cells (ES and iPS). These cells belong to the mesodermal layer, are dependent for their growth on attachment to a substrate and have a significant but finite growth capacity. <<MSC>> cells express a series of membrane markers such as CD44, CD29, CD73, CD105 and SSEA4 and are under certain experimental conditions able to form bone tissue, cartilage tissue and adipose tissue.

Mesodermal Stromal or Stem Cells (MSC Cells).

In adults, MSCs may be isolated from very numerous tissues. The first MSC cells were isolated from bone marrow. In a second phase, MSC cells were found in almost all the investigated tissues. These cells belong to the mesodermal layer and are dependent for their growth on attachment to a substrate and have a finite growth capacity. MSC cells express a series of membrane markers such as CD44, CD29, CD73 and under certain experimental conditions are capable of forming bone tissue, cartilage tissue and adipose tissue.

MSC or MSC Type Cells

MSC or MSC type cells mean mesodermal stem cells also known under the name of multipotent stroma cells, as well as cells having the same biological characteristics. MSC or MSC type cells in a non-limiting way include mesodermal progenitor cells (MePC) and mesodermal stromal or stem cells of adult tissue (MSC).

Muscle progenitor cells (<<MPC>>).

MPC cells stem and are isolated from muscle tissue. These cells are responsible for maintaining the muscle function and control the repair of muscle tissue. MPCs are capable of self-renewal in a limiting way and of forming muscle tissue ex vivo and in vivo.

Description of the Procedures for Isolating and Producing Cells for Screening, Derived from Human Pluripotent Cells (hES and iPS).

The cells may be produced from non-differentiated hES cells or iPS cells. The production conditions are the following and are identical for both cell types. The islets of non-differentiated cells which may be identified by their morphological characteristics form the basis of the cell material for producing cells.

Non-differentiated cell islets which may be identified on morphological criteria or on expression criteria such as the expression of Tra1-60 or the expression of GFP under the control of a gene promoter associated with maintaining pluripotency such as Oct4/pouf5 are mechanically dissociated under control of a binocular magnifier, by means of a needle. Mild enzymatic dissociation by using enzymes of the collagenase and trypsin type may also be used. It is also possible to add chelating agents of divalent ions such as EDTA and EGTA. In the latter case, the use of an inhibitor of the Rhoa protein (Rock inhibitor) allows better restarting of the thereby dissociated cells. The small clusters of cells obtained after dissociation are automatically counted or by means of an hematocytometer and the viabilities are estimated by using trypan blue exclusion or propidium iodide marking techniques. The following step is formed by the sowing of the cell aggregates on cell supports covered with collagen or with its derivatives such as gelatin. Other constituents of the extracellular matrix such as fibronectin, laminin, vitronectin, or synthetic compounds such as poly-ornithine may be used for this step. The cells are then cultivated in the presence of a culture medium of the DMEM type supplemented with glutamine, with a mixture of non-essential amino acids, of beta-mercaptoethanol and of bovine serum or from another origin such as human serum. The operation may be carried out in a completely synthetic medium without any protein of animal origin.

During this invention, it was able to be shown that the association of FGF with antioxidants such as derivatives of ascorbic acid increased both the robustness of the production method, the production kinetics and the amount of produced cells. By using this approach combining FGF with ascorbic acid 2-phosphate, differentiated cells derived from pluripotent cells were able to be produced in all the experiments with the different types of pluripotent cells whether these be hES cells or iPSes. Five days after sowing, it is possible to distinguish individual cells adhering to the cell substrate which emerge from cell clusters and then enter cell divisions. This is the first step of morphological differentiation. Between day 10 and 20, the cells are transplanted by using enzymatic solutions of the trypsin type combined with chelating agents of the EDTA types. It is also possible to use mechanical dissociation. The thereby obtained cells are sown on cell supports covered with collagen or with its derivatives of the gelatin type. Like for the first step, it is possible to use another type of substrate. This second step is the cell amplification step which allows an increase in the number of cells and homogenization of the thereby obtained cell population. As soon as the first transplantation, the presence of FGF associated with ascorbic acid 2-phosphate allows an increase in the number of cells by a factor 2 and then during the passages, the number of cells considerably increases in the presence of this combination. The difference may then attain several log factors. It is also possible to produce this type of cells in synthetic media containing FGF and antioxidants such as ascorbic acid and its derivatives. It is remarkable that the presence of FGF without any antioxidant does not allow an increase in the number of cells derived from pluripotent cells. The thereby obtained cells are preserved by standard methods such as cryopreservation with DMSO as cryopreservation agents. For this step, it is also possible to use glycerol, trehalose, glycine and arbutin as cryoprotective agents as well as commercial solutions. The preservation may be effected by vitrification. Cryopreservation of the produced cells has excellent yield and does not modify the biological parameters such as cell growth or the expression of surface markers. Under these production conditions, the cells keep their normal nature while having finite growth and a normal karyotype.

The described differentiation and amplification methods for the thereby produced cells have a similar efficiency for cells derived from hES or iPS. In both cases, the presence of the combination of FGF associated with ascorbic acid 2-phosphate in the culture medium dramatically increases the efficiency of the cell differentiation and amplification methods.

Characterization of Differentiated Cells Derived from Human Pluripotent Cells (hES and iPS) for Screening.

The first characterization steps are based on functional criteria such as the growth capacity, adhesion to the substrates and on morphological criteria. Morphologically, the produced cells have characteristics similar to those of mesenchymal cells. Their growth is dependent on the attachment to a substrate. Molecular analyses carried out show that the expression of the genes associated with the characteristic pluripotency condition of pluripotent cells such as Oct4, Nanog are undetectable in cells produced by RT-PCR techniques.

Analysis of surface markers by flow cytometry of the produced cells shows an absence of expression of SSEA3, of Tra-1-60, of Tra-1-80 which are membrane determinants associated with the pluripotency condition and a presence of membrane determinants such as CD73, CD44, CD166, CD105 and CD29. The expression of these markers is also present on multipotent stroma cells (MSC). MSC cells were individualized about ten years ago. The cells produced by the method of the invention therefore share certain properties of MSCs:

Adhesion to the substrates
High but finite growth potential
Preservation by freezing
Expression homogeneity for the CD73, CD29, CD44, CD166 markers.
Osteogenic differentiation potential.

The Combined Presence of FGF2 and of Ascorbic Acid 2-Phosphate in the Culture Medium Increases the Growth Capacity and the Expression of SSEA4 of the Cells Produced by the Method of the Invention.

In the method of the invention, with the presence of FGF2 and of ascorbic acid 2-phosphate, it is possible to produce differentiated cells from pluripotent cells. This increase in the growth capacities is associated with the specific expression of a membrane marker SSEA4. This membrane marker is also expressed by pluripotent cells and certain (neural or mesodermal) progenitor cells. It is remarkable to note that FGF2 and ascorbic acid 2-phosphate individually do not give the possibility of inducing expression of SSEA4 or of significantly increasing the proliferation capabilities. On the other hand, the presence of FGF2 and of ascorbic acid 2-phosphate together considerably increases the growth capacities and the expression of SSEA4 without modifying the expression of other markers associated with totipotency like Tra-1-60, Tra-1 80, SSEA3 and SSEA1. With the method of the invention, it is possible to homogeneously produce differentiated cells which express SSEA4. Under these production conditions described by the method of the invention, the differentiated cells have a significant proliferation capacity which is associated with the expression of SSEA4.

The Cells Produced by the Method of the Invention have a Sensitivity Specific to the Inhibitors of the Synthesis of Mevalonate Like the Inhibitors of HMG CoA Reductase.

Mevalonate is a precursor indispensable for the synthesis of metabolite cholesterol, key of cell activity. Statins, steric inhibitors of HMG CoA reductase (an enzyme which controls the synthesis of mevalonate) block the production of mevalonate and thus the production of cholesterol. With provision of mevalonate by the extra-cellular medium, it is possible to restore the production of cholesterol in spite of the presence of statin.

These properties give the possibility of building cell tests notably for predicting and analyzing the toxicity of the inhibitors of the synthesis of mevalonate. Certain cell types like MPC cells are particularly sensitive to statins. In this cell type, the statins are toxic and this toxicity is abolished by the presence of mevalonate in the presence of extra-cellular medium. It is thus possible to show by a simple cell test that statins are toxic through a mechanism which involves the synthesis of mevalonate.

Recent examples with the inhibitors of COX 2 and of HMG CoA reductase show that underestimating toxicological issues may have considerable consequences from a human, health and economical point of view. Defining predictive toxicology systems is therefore a critical goal. The inhibitors of HMG CoA reductase, including statins, have particular toxicity for muscle tissue. This toxicity may range from simple aches to rhabdomyolyses which may cause death.

Human muscle precursor cells (MPCs) are good indicators of muscle toxicity. Indeed, cell growth of MPCs is inhibited by the presence of statin in the growth medium. This inhibition is dose-dependent. The presence of mevalonate gives the possibility of totally lifting the inhibition of growth. This inhibition is therefore accomplished through the inhibition of HMG CoA reductase, an enzyme responsible for the production of mevalonate, a precursor in the synthesis of cholesterol.

The cell produced from pluripotent cells according to the method of the invention have a sensitivity comparable to the MPCs for the inhibitors of HMG CoA reductase. Indeed, the presence of inhibitors of HMG CoA reductase like novastatin or simvastatin in the culture medium reduces the number of differentiated cells derived from pluripotent cells in a dose-dependent way. This inhibition is raised by the presence of mevalonate. The thereby observed inhibition of growth is therefore due to the inhibition of the enzyme responsible for the production of mevalonate. The cells produced from embryonic stem cells and those produced from induced pluripotent cells have the same type of sensitivity to the inhibitors of HMG CoA reductase and to mevalonate.

The technology of iPSes gives the possibility of producing pluripotent cells from any individuals. The method of the invention gives the possibility of generating differentiated cells derived from iPS cells from patients having exacerbated sensitivity to the inhibitors of the synthesis of mevalonate. These cell tools will be useful for understanding the toxicity mechanisms and isolating markers for preventing and tracking this toxicity.

The cells produced by the method of the invention allow high throughput screening of the synthesis of mevalonate.

High throughput screening of compounds requires the possibility of cultivating the cells in formats compatible with this technology such as 96- or 384-well multiwell plates. On the other hand, the use of rapid systems for reading out the results, compatible with analysis robots, is also required. The cells produced by the method of the invention may be cultivated in 96- and 384-well multiwell plates. Under these conditions, the variation coefficients of cell counts are small. In a first phase, the number of cells obtained in multiwells was determined by directly counting the cells after marking by using image analysis systems. These analysis systems are accurate, but relatively slow. Tests based on the amount of ATP and mitochondrial activity were therefore developed. It was possible to demonstrate that for the cells produced by the method of the invention, there exists a linear relationship between the measured amount of ATP or mitochondrial activity and the number of cells per well. In other words, the amount of ATP or the measured mitochondrial activity is a measurement of the number of cells. A bank of chemical molecules of more than 1,200 compounds representing the main active products used in human clinical practice was screened.

The cells described by the method of the invention gave the possibility of screening this bank. These cells were cultivated in 96- and 384-well multiwells for three days in the presence and in the absence of mevalonate and in the presence of the different compounds of the bank. All these experiments were carried out with robots allowing distribution of the compounds and cultivation of the cells in a sterile medium. The compounds were selected on the following criteria: decrease the number of cells in the absence of mevalonate and maintaining the number of cells in the presence of mevalonate. With these criteria it is possible to sort out the molecules for which the toxicity is related to the inhibition of the synthesis of mevalonate. In all the screenings carried out, the inhibitors of HMG CoA reductase, a limiting enzyme for the synthesis of mevalonate used in human clinical practice, present in the bank, were able to be selected. These experiments were able to show that the cells produced according to the method of the invention allow screening of the inhibitors of the synthesis of mevalonate in a robust way by using high throughput screening technologies. This proof of feasibility gives the possibility of contemplating screenings with the thereby described systems of banks representing several hundred thousand different compounds. It should also be noted that the molecules are sorted out on a functional criterion, cell toxicity due to the inhibition of the synthesis of mevalonate. These types of tests will give the possibility of isolating other classes of inhibitors of the synthesis of mevalonate. With this system, it is possible to isolate novel inhibitors on their functional capacity independently of their direct interaction with HMG CoA reductase.

The cells produced by the method of the invention allow high throughput screening of compounds protecting against the toxic effect of the inhibitors of the synthesis of mevalonate.

The toxic effects of the inhibitors of the synthesis of mevalonate limit the use of this type of compound in clinical practice. Indeed, many secondary effects on muscular tissue are observed, most of which are limited and reversible. Nevertheless, in many cases, around 20% of the treated patients have muscular pains (myalgias, cramps). These effects very frequently cause interruptions in the treatment. Identifying compounds which may reduce the toxic effect of the inhibitors of the synthesis of mevalonate is a goal which may have clinical consequences. With this in mind, the screen is made by using the cells produced by the method of the invention which are treated with inhibitors of the synthesis of mevalonate such as the inhibitors of HMG CoA reductase. The screening conditions are produced as earlier and the cells are treated with an inhibitor of HMG CoA reductase, simvastatin or all the molecules of this drug class. The compounds are sorted according to their capability of reducing the toxic effects of simvastatin. By using this approach, about ten compounds were able to be selected in a bank of more than 1,200 compounds. These are potential candidates for reducing the toxic effects of this class of therapeutic molecules.

On the other hand, it was shown that the inhibitors of HMG CoA reductase induce the expression of a protein, atrogin, a protein involved in muscular atrophy phenomena. Muscular atrophy is associated with many pathologies (neuromuscular diseases, cancer, HIV, kidney failure, ageing or immobilization) and is per se a poor prognosis factor. The thereby described screen also allows isolation of compounds which may limit muscle atrophy. Indeed, treatment with inhibitors of HMG CoA reductase of the cells produced by the method of the invention gives the possibility of reproducing in the culture dish, a model of controlled cell atrophy. The compounds which limit toxicity, for the cells produced by the method of the invention, in the presence of inhibitors of HMG CoA reductase, are potential candidates for reducing muscular atrophy and treating sarcopenia. Sarcopenia is the loss of muscles due to ageing, to a neurological disease, to a viral disease (for example AIDS) or to a tumoral disease. This is a frequent disease for which there does not exist yet any specific therapeutic solutions.

The cells produced by the method of the invention allow high throughput screening of compounds enhancing the toxic effect of the inhibitors of the synthesis of mevalonate.

The possibility of predicting compounds enhancing cell toxicity in the presence of inhibitors of the synthesis of mevalonate should either allow preventing combinations of potentially toxic drugs for tissues such as the muscle tissue, or defining combinations of drugs having a cytotoxic effect useful for tumoral treatments. In human clinical practice, it has been frequently observed that the toxicity of inhibitors of HMG CoA reductase may be exacerbated by certain drug combinations. On the other hand, statins have been used for the past few years, for their cytotoxic properties in the treatment of certain forms of tumors (digestive tumors, breast tumors or lymphomas) and for their possible use as preventive agents (colon cancer or prostate cancer). In the large majority of the cases, in this latter indication, statins are used in combination with other anti-tumoral molecules.

With this in mind, the screen is made by using cells produced by the method of the invention which are treated with inhibitors of the synthesis of mevalonate such as inhibitors of HMG CoA reductase. The conditions of the screen are produced as earlier and the cells are treated with an inhibitor of HMG CoA reductase, simvastatin. The compounds are sorted according to their capability of enhancing the toxic effects of simvastatin. By using this approach, about fifteen compounds were able to be selected in a bank of more than 1,200 compounds. These are potential candidates for increasing the toxic effects of this class of therapeutic molecules. Among these compounds, some of them are agents already known for their cell toxicity and others are cytotoxic agents used in human clinical practice as anti-tumoral agents. On the other hand, scientific and clinical data indicate that there exists tumoral stem cells which are on the one hand responsible for resistance phenomena observed in conventional anti-tumoral treatments. These tumoral <<stem cells>> are the result of a transition from <<epithelial>> tissue to <<mesodermal>> tissue. The transition towards the mesodermis of tumoral epithelial cells gives these cells a growth advantage and a larger capacity for forming tumors. Tumoral <<stem cells>> have certain features common to the differentiated <<MSC>> cells derived from pluripotent cells. Indeed, the <<MSC>> cells are derived from pluripotent cells which are organized as an epithelium for evolving towards a mesodermal tissue. During the differentiation, they undergo a transition from the epithelial type to the mesodermal type. Further, <<MSC>> cells express at a high level the marker CD44 which is also expressed by tumoral <<stem>> cells. With these arguments, it is possible to believe that <<MSC>> cells derived from pluripotent cells represent a model of <<tumoral stem>> cells in vitro. The described screening then allows isolation of the compounds having a specific activity against the tumoral <<stem>> cells. With the screening sorting out the molecules which specifically enhance the toxicity of statins, it is possible to establish a rational strategy for defining the molecules which have to be associated with statins for increasing their anti-tumoral potential and for targeting the <<tumoral stem>> cells.

The use of the cells produced by the method of the invention in the presence or in the absence of an inhibitor of the synthesis of mevalonate, in the presence or in the absence of mevalonate, allows high throughput screening of the compounds for:
- inhibiting the synthesis of mevalonate
- attenuating the secondary effects of inhibitors of HMG CoA reductase
- preventing drug interactions having muscular toxicity effects
- reducing muscle atrophy
- potentializing cytotoxic effects inhibiting HMG CoA reductase and defining drug combinations for their antitumoral activity and in particular against tumoral <<stem>> cells.

The therapeutic applications of the thereby sorted out compounds are very vast: hypercholesterolemias, muscle atrophies as well as tumoral diseases.

Example 1

FGF2 Combined with Ascorbic Acid Improves the Robustness and Efficiency of the Techniques for Producing Differentiated MSC Cells or of the MSC Type Derived from Human Embryonic Stem Cells (hES) Having the Characteristics of Multipotent Stroma Cells (MSC)

Introduction

Multipotent stroma cells or MSCs have been individualized, about ten years ago. The ISCT (International Society for Cell Therapy) defines these cells on several types of criteria:
- Functional criteria: growth in a culture and substrates such as culture plastic.
- Identity criteria: absence of expression of CD45 and of CD34 and expression of CD73, CD29 and CD44.
- Differentiation potential in the osteogenic, chondrocyte and adipose lineage.

In a first phase, the MSCs were isolated from bone marrow. Subsequently, these cells were partly purified from many tissues such as adipose tissue, peripheral blood, liver, lungs, muscles, placenta, amniotic liquid or umbilical cord blood. MSCs are involved in tissue repair including bone repair, in immunomodulation, in the control of angiogenic response and in the tumoral phenomenon.

These features make MSCs indispensable cell tools for toxicological studies within the musculo-skeletal sphere and for discovering new therapeutic routes in different fields (orthopedics, vascular diseases, inflammatory diseases, cancer and gene transfer).

The isolation and production of stem cells from human tissues however have many limitations:
- Accessibility of human tissue samples
- Isolation and production conditions which have to be adapted for each of the tissues.
- Limited growth capacity.
- Phenotype instability
- Interindividual variability The existence of human pluripotent stem cells gives the possibility of accessing normal human cells without any limitations. There exist two types of pluripotent cells: embryonic stem cells (hES) and induced stem cells (iPS). The essential features of pluripotent cells are the capability of self-renewal without any limitations and the possibility of differentiation into all the cell types making up an entire organism.

The possibility since the work of J. Thompson (Thompson et al. 1998) of using human embryonic stem cells (hES) has opened very many possibilities, some of which may have clinical implications. Both essential features which are the capability of self-renewal without any limitations and the capability of differentiation into all the cell types making up an adult organism makes these cells an extremely useful tool. Experimentally, human embryonic stem cells have allowed development of differentiation procedures and isolation of many types of cells (cardiac cells, smooth muscle cells, neural cells, keratinocytes, hematopoietic cells, insulin-producing cells).

A) Description of the Procedures for Isolating and Producing Cells of the MSC Type Having Features Common to MSCs Derived from Human Embryonic Stem Cells (hES).

The cells are produced from non-differentiated hES cells.

The production conditions are the following. The islets of non-differentiated cells which may be identified by their morphological characteristics are the basis of the cell material for producing these cells.

1) Mechanical transplantation of the islets recognized by the morphology of hES cells.
   a. Change the hES cell dishes for EB medium (see Table 1);
   b. Striate with a needle and then detach the aggregates. The 29G needle is mounted on a 1 mL syringe. Select the colonies without any sign of morphological differentiation. Several tens of colonies are thereby isolated. The colonies are counted in the presence of trypan blue for appreciating their viability;
   c. Centrifugation at 900 rpm for 1 minute for forming pellets without crushing them, in 15 mL tubes;
   d. Take up the pellet into 1 mL of EB medium. Suck up, discharge for partly dissociating the cell aggregates. The size of the aggregates should be of several tens of cells;
   e. Trypan blue counting: determination of the number of aggregates and viability.

2) Selection and amplification of MSC cells:
   f. A specific number of aggregates (several tens of them) is sown in the EB medium on gelatinized culture dishes. 50 to 200 aggregates are sown per 25 cm$^2$ flasks;
   g. The first change is carried out after 48 hours and then every 2 to 3 days. Two culture conditions are tested. Under the first condition, the source of growth factors is limited to fetal calf serum (EB medium). For the second, FGF2 (10 ng/ml) and 1 mm of ascorbic acid 2-phosphate are added to the fetal calf serum. This medium is called EBMOD.
   h. After 4 to 5 days, the cells emerge from the aggregates, bind to the substrate and start to divide.
   i. Between day 10 and day 15, the cells are transplanted by using a solution of trypsin combined with EDTA.
   j. After washing with culture medium by centrifugation and counting, the cells are sown on gelatinized supports with a density ranging from 2,000 cells to 10,000 cells per cm$^2$.
   k. The first transplantations are carried out between day 5 and 10.

Within the scope of this procedure, we compared two culture media: the medium which we called EB and a medium EBMod to which we added FGF2 at a concentration of 10 µg/ml and Ascorbic Acid 2-Phosphate (AA2P) at the concentration of 1 mM. The composition of the EB medium is indicated in Table 1.

TABLE 1

Composition of the EB medium

| | Stock concentration | Final concentration | Volume (total of 500 ml) |
|---|---|---|---|
| KO-DMEM | | sfc 500 ml | 390 ml |
| PCS (Fetal calf serum) | 100% | 20% | 100 ml |
| β-mercaptoethanol | 50 mM | 50 μM | 500 μl |
| Glutamax | 200 mM | 2 mM | 5 ml |
| NEAA (MEM aa not essential) | 100X | 1X | 5 ml |
| Penicillin/Streptomycin | 10000 IU/ml | 10 IU/ml | 500 μl |

For this study, hES embryonic stem cells WT4 (KCL-002), XY were used. This hES cell line was isolated by Stephen Minger from the Wolfson Centre for Age-Related Diseases, King's College London. It stems from the UK Stem Cell Bank: UK Stem Cell Bank, National Institute for Biological Standards and Control. Similar results are obtained with SA01 embryonic stem cells. This procedure is also applicable to embryonic stem cells which have mutations which represent pathological models.

B) Production of Differentiated Cells of the MSC Type Sharing Characteristics of Multipotent Stroma Cells (MSC) Derived from Human Embryonic Stem Cells (hES).

The two conditions of media were analyzed on the production and the characterization of cells obtained according to the procedure described earlier. In this case, the differentiated cells of the MSC type were derived from WT4 human embryonic stem cells. The results are indicated in the two following tables.

TABLE 2

Results of a growth curve obtained in the absence of FGF2 and AA2P

| MSWT4 | Number of cumulated divisions | Number of accumulated cells |
|---|---|---|
| D 0 | | |
| D 10 | ND | $7.7 \, 10^5$ |
| D 17 | ND | $6.6 \, 10^5$ |
| D 24 | 1.15 | $1.7 \, 10^6$ |
| D 30 | 4.02 | $1.2 \, 10^7$ |
| D 38 | 6.18 | $5.6 \, 10^7$ |
| D 43 | 7.86 | $1.8 \, 10^8$ |
| D 76 | 6.54 | $7.2 \, 10^7$ |

TABLE 3

Results obtained in the presence of FGF2 and AA2P

| MSC WT 4 FGF2 AA2P | Number of cumulated divisions | Number of cumulated cells |
|---|---|---|
| D 0 | | |
| D 10 | ND | $1.5 \, 10^6$ |
| D 17 | 2.96 | $1.2 \, 10^7$ |
| D 21 | 4.54 | $3.6 \, 10^7$ |
| D 23 | 6.1 | $1 \, 10^8$ |
| D 30 | 9.6 | $1.2 \, 10^9$ |
| D 38 | 13.3 | $1.6 \, 10^{10}$ |
| D 43 | 16.7 | $1.6 \, 10^{11}$ |
| D 48 | 21.3 | $4 \, 10^{12}$ |
| D 52 | 24.8 | $4.5 \, 10^{13}$ |
| D 59 | 30.6 | $2.5 \, 10^{15}$ |
| D 65 | 36 | $1 \, 10^{17}$ |
| D 71 | 40 | $1.8 \, 10^{18}$ |
| D 78 | 43 | $1.4 \, 10^{19}$ |
| D 87 | 44.5 | $3.8 \, 10^{19}$ |
| D 94 | 45.5 | $7.6 \, 10^{19}$ |
| D 101 | 48.6 | $6.5 \, 10^{20}$ |
| D 118 | 50.2 | $1.9 \, 10^{21}$ |

Under both medium conditions, it is possible to derive adhering cells which are capable of multiplying under both culture conditions. In the absence of FGF and of ascorbic acid 2-phosphate, the number of isolated cells is much less significant. These cells after a few cell divisions become senescent and are incapable of being efficiently amplified under these conditions. The amount of cells obtained is more substantial in the presence of the medium containing FGF and ascorbic acid 2-phosphate. Under the latter conditions, the number of cells may be increased by several log factors. The introduction of this modification also allows shortening of the production times for cells of the MSC type. Under these conditions, from about 100 aggregates stemming from human embryonic stem cells, it is possible to produce $10^8$ cells within 23 days of cultures which have a significant replicative potential (more than about thirty cell divisions). It should be noted that these modifications do not alter the capability of these cells of entering a senescence phase, indicating the non-transformed nature of the thereby produced cells. It should be noted that under these conditions, it is possible to produce MSC cells with all human normal embryonic stem cells or having mutations. This method was applied successfully for embryonic stem cells from embryos affected with Steinert's disease. These conditions give the possibility of increasing the robustness of the method for producing differentiated cells of the MSC type derived from human embryonic stem cells.

C) Characterization of Differentiated Cells of the MSC Type Derived from Human Embryonic Stem Cells (hES) by Flow Cytometry.

The characterization of differentiated cells produced by the production method from human embryonic stem cells (hES) was carried out by flow cytometry. This common technology allows qualitative and quantitative analyses of the molecules present at the surface of the cells by using specific antibodies. For this step, antibodies directed against the membrane markers associated with totipotency conditions and against markers of MSC cells were used. The thereby produced cells do not express at their surfaces the antigen TRA 1-60 which is associated with totipotency conditions. Similar results are obtained with antibodies directed against other markers of totipotency such as SSEA3 and TRA 1-80. These are therefore cells having lost their specific pluripotent nature of embryonic stem cells. On the other hand, these cells express markers associated with MSC cells such as CD73, CD29, CD44, CD166 and CD105. The results obtained are shown in Table 4.

TABLE 4

Flow cytometry analysis of membrane markers of MSC cells

| Antibody | Fluorescence intensity | % of positive cells |
|---|---|---|
| CD73 | 400 | 99% |
| CD29 | 672 | 100% |
| CD44 | 624 | 100% |
| CD166 | 145 | 98% |

TABLE 4-continued

Flow cytometry analysis of membrane markers of MSC cells

| Antibody | Fluorescence intensity | % of positive cells |
|---|---|---|
| CD105 | 283 | 95% |
| SSEA-1 | 567 | 1% |

The cells produced by the production method are homogeneous to more than 95% for the markers CD73, CD29, CD44, CD166 and CD105. These results are not modified by the presence of FGF2 and AA2P. The thereby produced cells have the main characteristics of MSC cells for their surface markers.

D) the Combined Presence of FGF2 and Ascorbic Acid 2-Phosphate in the Culture Medium Increases the Growth Capacity and the Expression of SSEA4 in Cells Produced by the Method of the Invention.

The role of FGF2 and of ascorbic acid 2-phosphate on the growth capacities of the isolated cells according to the method of the invention was analyzed on cells derived from human embryonic stem cells SA01. The cells are cultivated in the presence of 20% fetal calf serum (control condition) and in the presence or in the absence of FGF2 and of ascorbic acid 2-phosphate (AA2P). The results which represent the maximum number of cells obtained before entering senescence are indicated in the following Table 5.

TABLE 5

|  | Control (FCS20%) | Control (FCS20%) FGF2 10 ng/ml | Control (FCS20%) AA2P 1 mM | Control (FCS20%) FGF2 10 ng/ml + AA2P 1 mM |
|---|---|---|---|---|
| Maximum number of cells before senescence | $7 \cdot 10^8$ | $4.7 \cdot 10^{13}$ | $3.7 \cdot 10^{15}$ | $1.5 \cdot 10^{20}$ |

The combined presence of FGF2 and AA2P gives the possibility of increasing by about a log factor of 12, the amount of accumulated maximum cells. FGF2 and ascorbic acid individually have a much smaller effect on the increase in the amount of cells, a little less than 5 log factors for FGF2 and a little less than 6 log factors for ascorbic acid 2-phosphate. The effect of FGF2 and of the ascorbic acid is clearly synergistic on the maximum cell amount of accumulated cells.

SSEA4, a membrane marker, is expressed on the pluripotent cells and on a certain number of progenitor cells from different tissues such as marrow, adipose tissue or neural tissue.

The presence of SSEA4 on cells cultivated under these different conditions were analyzed by flow cytometry by using a specific antibody directed against SSEA4. The results are indicated in the following Table 6:

TABLE 6

|  | Control (FCS20%) | Control (FCS20%) FGF2 10 ng/ml | Control (FCS20%) AA2P 1 mM | Control (FCS20%) FGF2 10 ng/ml + AA2P 1 mM |
|---|---|---|---|---|
| Average fluorescence intensity | 7 | 10 | 7 | 26 |

Neither FGF2 nor ascorbic acid 2-phosphate significantly increase the expression of SSEA4. On the other hand, the combination of both molecules increases the amount of SSEA4 by a factor of 3.7. This fluorescence level is comparable with the one observed with human pluripotent cells. The combined presence of FGF2 and ascorbic acid 2-phosphate increased in a combined way the maximum number of accumulated cells and the expression level of SSEA4.

E) the Cells of the MSC Type Produced According to the Method of the Invention have a Normal Karyotype.

The karyotype of <<MSC>> cells was analyzed on chromosomes in a metaphase and proved to be without any detected abnormality in the presence and in absence of FGF2 and AA2P.

F) the MSC Type Cells Produced According to the Method of the Invention have Osteogenic Potential.

In an osteogenic medium, cells of the MSC type produced according to the method of the invention are capable of expressing functions of bone tissue. After 14 days of cultivation in a medium comprising dexamethasone, B glycerophosphate, the cells of the MSC type produced according to the method of the invention express alkaline phosphatase and form mineralization nodules. The mineralization nodules are revealed by a specific histochemical technique, Von-Kossa's staining.

G) Freezing Differentiated Cells of the MSC Type Derived from Human Embryonic Stem Cells (hES).

The thereby produced cells may be kept by freezing them. The freezing medium is the following: 90% of serum and 10% of DMSO. Freezing of the cells produced in the medium in the presence of FGF2 and AA2P was practiced at passage 7 and at a concentration of $10^6$ per ml.

The MSC cells produced under both conditions are very efficiently preserved by freezing. The freezing does not change the growth characteristics of MSC cells. These freezing techniques give the possibility of storing a large number of cells without modifying their biological characteristics.

H) Conclusions

The presence in the medium for amplifying differentiated MSC cells derived from hES cells with FGF2 and ascorbic acid 2-phosphate gives the possibility of:

increasing the robustness of the techniques for producing the differentiated cells from embryonic stem cells accelerating the production of these cells increasing the maximum number of produced cells increasing the proliferation potential obtaining cells having a normal karyotype specifically expressing SSEA4 as a marker of totipotent cells and of progenitor cells The cells produced in the medium in the presence of FGF2 and ascorbic acid 2-phosphate have characteristics associated with MSC cells:

Adhesion to the substrates

High but finite growth potential

A karyotype without any detectable abnormality.

Preservation by freezing

Homogeneity of expression for the markers CD73, CD29, CD44, CD166, CD 105.

Osteogenic potential

Example 2

FGF2 Associated with Ascorbic Acid Improves the Robustness and the Efficiency of the Techniques for Producing Differentiated Cells of the MSC Type Derived from Human Pluripotent Cells (iPS) Having Characteristics of MSC Cells A) Description of the Procedures for Isolating and Producing Cells Having Characteristics Common with Those of MSCs from Induced Pluripotent Human Cells (IPS).

The iPS cells iPS4603C15 and iPS4603PC1A were produced from human primary fibroblasts by using Yamanaka's procedure which introduces the following genes: Oct4, Sox2, cMyc and Klf 4. The gene transfer was carried out with retroviruses of the Moloney type. Viral transduction was carried out by co-infection with the 4 viruses bearing each of these 4 genes. Treatment by valproic acid allowed an increase in the efficiency of the reprogramming. After transduction, the cells are cultivated in the presence of nutritive tissue consisting of mouse embryonic fibroblasts in a calcium medium promoting emergence of human pluripotent cells. The essential constituent of the specific medium for growing pluripotent human cells is FGF2. The medium is changed every 24 hours. After 2 to 3 weeks, the first colonies having the characteristics of pluripotent cells are visible. These colonies are then isolated and mechanically transplanted. Two populations are then built up: a monoclonal population (iPS iPS4603C15) and a polyclonal population (iPS4603PC1A). The thereby isolated cells have the following characteristics:

- Extinction of the transduced exogenous genes used for reprogramming.
- Expression of totipotency markers: SSEA4 and TRA-1-81, TRA 1-60
- Normal karyotype
- Growth capacity while maintaining the pluripotency condition in the medium in the presence of FGF2
- Differentiation capacity after forming embryonic bodies (ectodermis, endodermis, mesodermis)

These cells have characteristics of induced pluripotent cells (iPS). These cells were therefore used for producing cells of the MSC type.

The production conditions are the following. The islets of non-differentiated cells which may be identified by their morphological characteristics are the basis of the cell material for producing these cells.

1) Mechanical transplantation of islets recognized by the morphology of hES cells
   l. Change the iPS cell dishes for EB medium (see Table 1).
   m. Striate with a needle and then detach the aggregates. The 29G needle is mounted on a 1 ml syringe. Select the colonies without any signs of morphological differentiation. Several tens of colonies are thereby isolated. The colonies are counted in the presence of trypan blue for appreciating their viability.
   n. Centrifugation at 900 rpm for 1 minute in order to form pellets without crushing them, in 15 ml tubes
   o. Take the pellet into 1 ml of EB medium. Suck up, discharge, for partly dissociating the aggregates of cells. The size of the aggregates should be of a few tens of cells
   p. Trypan blue counting: Determination of the number of aggregates and viability.

2) Selection and amplification of cells of the MSC type
   q. A specific number of aggregates (several tens of them) is sown in the EB medium on gelatinized culture dishes. 50 to 200 aggregates are sown per 25 cm² flask.
   r. The first change is carried out after 48 hours and then every 2 to 3 days. Two culture conditions are tested. Under the first condition, the growth factor source is limited to fetal calf serum (EB medium). For the second condition, FGF2 (10 ng/ml) and 1 mM of ascorbic acid 2-phosphate are added to the fetal calf serum. This medium is called EBMOD
   s. After 4 to 5 days, the cells emerge from the aggregates, bind to the substrate and start to divide.
   t. Between day 10 and 15, the cells are transplanted by using a solution of trypsin combined with EDTA.
   u. After washing with the culture medium by centrifugation and counting, the cells are sown on gelatinized supports with a density ranging from 2,000 cells to 10,000 cells per cm².
   v. The first transplantations are carried out between day 5 and 10.

Within the scope of this procedure, we compare two culture mediums: the medium which we called EB and a medium EBMod to which FGF2 was added at a concentration of 10 µg/ml and ascorbic acid 2-phosphate at a concentration of 1 mM. The composition of the EB medium is indicated in Table 1.

TABLE 7

Composition of the EB medium

| | Stock concentration | Final concentration | Total of 500 ml |
|---|---|---|---|
| KO-DMEM | | qsp 500 ml | 390 ml |
| FCS (Fetal calf serum) | 100% | 20% | 100 ml |
| β-mercaptoethanol | 50 mM | 50 µM | 500 µl |
| Glutamax | 200 mM | 2 mM | 5 ml |
| NEAA (MEM aa not essential) | 100X | 1X | 5 ml |
| Penicillin/Streptomycine | 10000 IU/ml | 10 IU/ml | 500 µl |

B) Production of Differentiated Cells Showing Characteristics of Multipotent Stroma Cells (MSC) from Induced Pluripotent Human Cells (iPS).

Both medium conditions were analyzed on the production and characterization of the cells obtained by following the procedure identical with the one described in Example 1

From the tenth day, the number of cells observed is larger in the medium in the presence of FGF and ascorbic acid 2-phosphate. This trend is confirmed during cultivation. The obtained results are indicated in the following table.

TABLE 8

Growth curve in the absence of FGF2 and AA2P

| MSC 4603 Cl 5 | Number of cumulated divisions | Number of cumulated cells |
|---|---|---|
| D 0 | ND | ND |
| D 10 | ND | ND |
| D 20 | 2.2 | $1.1 \cdot 10^6$ |
| D 24 | 4.5 | $5.3 \cdot 10^6$ |
| D 29 | 7.6 | $4.8 \cdot 10^7$ |
| D 38 | 12.1 | $1 \cdot 10^9$ |
| D 45 | 15.9 | $1.4 \cdot 10^{10}$ |
| D 52 | 18.2 | $7.4 \cdot 10^{10}$ |
| D 57 | 20.1 | $2.8 \cdot 10^{11}$ |

TABLE 8-continued

Growth curve in the absence of FGF2 and AA2P

| MSC 4603 Cl 5 | Number of cumulated divisions | Number of cumulated cells |
|---|---|---|
| D 66 | 22.2 | $1.1\ 10^{12}$ |
| D 80 | 23.9 | $3.7\ 10^{12}$ |
| D 87 | 25.4 | $1\ 10^{13}$ |

TABLE 9

Growth curve in the presence of FGF2 and AA2P

| MSC 4603 Cl 5 FGF2 AA2P | Number of cumulated divisions | Number of cumulated divisions |
|---|---|---|
| D 0 | ND | ND |
| D 10 | ND | ND |
| D 13 | 0.3 | $9.7\ 10^5$ |
| D 17 | 2.4 | $4.2\ 10^6$ |
| D 22 | 7.1 | $1.1\ 10^8$ |
| D 27 | 11 | $1.6\ 10^9$ |
| D 31 | 15 | $2.5\ 10^{10}$ |
| D 38 | 20.6 | $1.2\ 10^{12}$ |
| D 44 | 25.9 | $4.8\ 10^{13}$ |
| D 50 | 31 | $1.7\ 10^{15}$ |
| D 55 | 35.9 | $5\ 10^{16}$ |
| D 60 | 38.7 | $3.6\ 10^{17}$ |
| D 64 | 42.3 | $4.2\ 10^{18}$ |
| D 71 | 47.3 | $1.3\ 10^{20}$ |
| D 78 | 51.7 | $2.9\ 10^{21}$ |
| D 85 | 56.3 | $6.7\ 10^{22}$ |
| D 92 | 59.7 | $7.1\ 10^{23}$ |

Under both medium conditions, it is possible to derive adhering cells which are capable of multiplying under both cultivation conditions. However it should be noted that the amount of cells obtained is larger in the presence of the medium containing FGF and ascorbic acid 2-phosphate. Under the latter conditions, the number of cells may be increased by several log factors. The introduction of this modification also allows shortening of the times for producing cells of the MSC type. Under the latter conditions, from about 100 aggregates stemming from human embryonic stem cells, it is possible to produce $10^8$ cells within 22 days of cultivation which have significant replicative potential (of more than about thirty cell divisions).

In the absence of FGF2 and of ascorbic acid 2-phosphate, the number of isolated cells is much less significant. After three weeks of cultivation, the number of cells obtained is twenty times less significant. After 50 days of cultivation, the difference is $10^5$. After about twenty cell divisions, the cells produced under these conditions become senescent.

These results obtained with a clone of iPS cells are confirmed with a polyclonal population of iPS cells. The results obtained with a polyclonal population are similar.

C) Freezing Differentiated Cells Sharing the Characteristics of Cells of the MSC Type Derived from Induced Pluripotent Human Cells (IPS).

The thereby produced cells may be preserved by freezing. The freezing medium is the following: 90% of serum and 10% of DMSO. Freezing of the cells produced in an EBMod medium was practiced in passage 7 and at the concentration of $10^6$ per ml. The viability is measured by an exclusion test with trypan blue.

The MSC cells produced under both conditions are very efficiently preserved by freezing. Freezing does not modify the growth characteristics of the MSC cells. These freezing techniques give the possibility of storing large numbers of cells without modifying their biological characteristics.

D) MSC Cells Produced According to the Method of the Invention have Normal Karyotype.

The karyotype of MSC cells was analyzed on chromosomes in a metaphase and proved to be without any detectable abnormality in the presence and in the absence of FGF2 and AA2P.

E) Characterization of Differentiated Cells Sharing the Characteristics of Multipotent Stroma Cells <<MSC>> from Induced Pluripotent Human Cells (iPS) by Flow Cytometry.

The characterization of the differentiated cells produced by the production method from human embryonic stem cells (hES) was carried out by flow cytometry. This current technology allows qualitative and quantitative analyses of the molecules present at the surface of the cells by using specific antibodies. For this step, antibodies directed against markers of membranes associated with the totipotency condition and against markers of MSC cells were used. The thereby produced cells do not express at their surfaces, the antigen TRA 1-60 which is associated with the totipotency condition. The other totipotency markers like SSEA3 and TRA 1-80 give similar results. These are therefore cells having lost the specific pluripotent nature of the embryonic stem cells. On the other hand, these cells express markers associated with MSC cells such as CD73, CD29, CD44, CD166 and CD 105.

The obtained results are shown in Table 10.

TABLE 10

Flow cytometry analysis of membrane markers of MSC cells

| Antibody | Fluorescence intensity | % of positive cells |
|---|---|---|
| CD73 | 490 | 93% |
| CD29 | 742 | 93% |
| CD44 | 897 | 99% |
| CD166 | 228 | 97% |
| CD105 | 198 | 98% |
| SSEA-1 | 326 | 1% |

The cells produced by the production method are homogeneous to more than 93% for the markers CD73, CD29, CD44, CD166 and CD105. The thereby produced cells have the main characteristics of MSC cells for their surface markers.

Identical results are obtained with populations of polyclonal iPS cells. The thereby described procedure gives the possibility, with similar results, of obtaining differentiated MSC cells by using iPS cells obtained with the technique described by Thompson. The efficiency of the procedure described does therefore not depend on reprogramming techniques.

F) the Combined Presence of FGF2 and Ascorbic Acid 2-Phosphate in the Culture Medium Increases the Growth Capacity and the Expression of SSEA4 by the Cells Produced by the Method of the Invention.

SSEA4, a membrane marker is expressed on pluripotent cells and on a certain number of progenitor cells from different tissues such as marrow, adipose tissue or neural tissue.

The presence of SSEA4 on cells cultivated under these different conditions was analyzed by flow cytometry by using a specific antibody directed against SSEA4. The results obtained with cells derived from pluripotent cells induced from human fibroblasts (iPS iPS4603C15) are indicated in the following table:

TABLE 11

| 4 | % of positive cells | Average fluorescence |
|---|---|---|
| Control FCS 20% | 35.6% | 132 |
| Control FCS 20% + FGF2 10 ng/ml + AA2P 1 mM | 79.6% | 336 |

The presence of the combination of FGF2 and ascorbic acid 2-phosphate increases the number of cells expressing SSEA4 and the average fluorescence intensity.

The combined presence of FGF2 and ascorbic acid 2-phosphate increases together the maximum number of accumulated cells and the expression level of SSEA4.

G) the Cells of the MSC Type Produced According to the Method of the Invention have Osteogenic Potential.

In an osteogenic medium, the cells of the MSC type produced according to the method of the invention are capable of expressing functions of bone tissue. After 14 days of cultivation in a medium comprising dexamethasone, B glycerophosphate, the cells of MSC type produced according to the method of the invention express alkaline phosphatase and form mineralization nodules. The mineralization nodules are revealed by a specific histochemical technique: Von Kossa's staining.

H) Conclusions

The presence of FGF2 and of ascorbic acid 2-phosphate in the medium for amplifying the cells gives the possibility of:

Increasing the robustness of the techniques for producing differentiated cells from induced pluripotent cells (iPS)
Accelerating the production of these cells
Increasing the number of produced cells
Increasing the proliferation potential without modifying their capability of senescence.
Obtaining cells having a normal karyotype
Specific expression of SSEA4, a marker of totipotent cells and of progenitor cells.

The cells produced in the medium and in the presence of FGF2 and ascorbic acid 2-phosphate have the characteristics associated with MSC cells:

Adhesion to the substrates
High but finite growth potential.
Preservation by freezing
Homogeneity of expression for the markers CD73, CD29, CD44 and CD166.
Osteogenic potential Example 3

Differentiated Cells of the MSC Type Derived from Human Embryonic Stem Cells (hES), Tools for Predictive Toxicology of Muscular Tissue for High Throughput Screening Techniques A) Human Muscle Precursor Cells (MPC): Tools for Predictive Toxicology.

Human muscle precursor cells (MPC) are good indicators of muscular toxicity. Indeed, the cell growth of MPCs is inhibited by the presence of statin in the growth medium. This inhibition is dose-dependent. The presence of mevalonate allows the inhibition to be totally raised. This inhibition is therefore accomplished through the inhibition of HMG CoA reductase, an enzyme responsible for the production of mevalonate, a precursor in the synthesis of cholesterol. With this cell test system, the toxicity of different statins, having been used in human clinical practice, has been tested. The obtained results are indicated in the patent: culture composition, culture method and their uses in PCT WO 2004/0055174 A1.

At a concentration of 1 µM, the whole of the statins have toxicity for muscle cells. This toxicity is also dependent on the type of statin. Cerivistatin has a greater toxicity at all the tested concentrations. These results are in good correlation with clinical observations which have shown a significant toxicity of cerivistatin which was withdrawn from the market for its significant muscular toxicity. This cell test (bioassay) using MPCs therefore has a predictive value for muscular toxicology. However, there exists intrinsic limitations to this type of bioassay which are related to the biological characteristics of MPC cells. MPC cells are human primary cells isolated from muscle tissue which have variations from batch to batch, limited replication capacities and phenotype instability during the passages.

B) Differentiated Cells of the MSC Type Derived from Human Embryonic Stem Cells as Tools for Predictive Toxicology.

The goal is therefore to replace MPC cells with cells which may be produced in a reproducible way in a large amount and having sensitivity to inhibitors of HMG CoA reductase. Differentiated cells of the MSC type derived from pluripotent human cells (hES and iPS) may be produced without any limitations on number (see Example 1). Table 2 indicates that these cells have sensitivity to statins close to the one observed with MPC cells. Differentiated cells of the MSC type derived from hES cells (SA01) designated as: <<MSC>> SAMU 43, are cultivated with increasing doses of Mevolin (Lovostatin) and of Simvastatin in the presence and absence of mevalonate. After 7 days of cultivation, the cells are set, stained and then counted by image analysis. The obtained results are shown in the following table:

TABLE 12

Dose response curves of « MSC » SAMU43: effect of mevalonate

| | Concentration in M | | | | | |
|---|---|---|---|---|---|---|
| | 0 | $5\ 10^{-6}$ | $10^{-6}$ | $5\ 10^{-7}$ | $10^{-7}$ | $5\ 10^{-8}$ |
| Mevinolin | 9842 | 122 | 3232 | 6934 | 10021 | 10167 |
| Simvastatin | 9553 | 45 | 1750 | 5938 | 10215 | 9467 |
| Mevinolin + Mevalonate | 8223 | 8148 | 9525 | 9003 | 9423 | 9270 |
| Simvastatin + Mevalonate | 9699 | 9281 | 8991 | 9310 | 8834 | 8408 |

The <<MSC>> SAMU43 cells are sensitive to statins in a dose-dependent way. Like for MPCs, the presence of mevalonate prevents toxicity of the statins. The observed toxicity is therefore due to the inhibition of the synthesis of mevalonate, a precursor of cholesterol. It is therefore possible to use differentiated cells of the MSC type derived from embryonic stem cells for evaluating cell toxicity of the inhibitors of the synthesis of mevalonate. These differentiated cells of the MSC type derived from embryonic stem cells are therefore an unlimited source for this type of cell test.

C) Differentiated Cells of the MSC Type Derived from Embryonic Stem Cells: Tools for Screening.

The development of high throughput screening technology requires the possibility of cultivating the cells in multiwells without altering the biological functions and having automatable read-out systems. With ATP dosage, it should be possible to determine the number of cells automatically.

In this test, the light emission is proportional to the amount of cell ATP. The following experiments allowed verification of the relationship between the amount of ATP and the number of cells. Increasing numbers of cells were either analyzed by image analysis or by determining the amount of ATP. The cells were cultivated in 96-well multiwells. From $10^2$ cell to $10^4$ cells were analyzed by image analysis and by dosage of the ATP amounts.

There exists a good linearity between the number of cells determined by the image analysis and the amount of detected ATP by luminescence with an excellent $R^2$ of 0.9831. Determination of the number of cells by the ATP amount is therefore possible. This approach allows automated readout of the number of cells. Similar results are obtained by using traces of mitochondrial activity. Differentiated cells of the MSC type, derived from hES cells, <<MSC>> WT, were sown on 384 multiwells gelatinized beforehand by using a distribution robot of the Bravo type, at the concentration of 2,000 cells per well. The amount of cells was evaluated by Cell Titer Glow after 72 hours of cultivation in the presence or in the absence of simvastatin in a culture medium containing 20% of fetal calf serum. The obtained results are indicated in Table 4.

TABLE 13

Toxicity of simvastatin for MSCs derived from embryonic stem cells in 384-well multiwells.

|  | DMSO 0.2% | CV DMSO 0.2% | Statin 2 µM | CV Statin 2 2 µM | DMSO/ Statin |
|---|---|---|---|---|---|
| « MSC» WT | 987206 | 5.4 | 474583 | 15.9 | 2.08 |

CV means coefficient of variation, which is the standard deviation divided by the average.

Simvastatin is toxic for differentiated cells at 2 µM with a <<DMSO over statin>> ratio of more than 2. The coefficients of variation are not very high, between 2.9 and 15.9.

Toxicity is not limited to simvastatin, but is also observed with two other statins. In all the cases, this toxicity is abolished by mevalonate indicating that this inhibition is accomplished so that the inhibition of HMG CoA reductase, an enzyme responsible for the synthesis of mevalonate. For this experiment, the differentiated <<MSC>> SA01 cells derived from hES cells (SA01) were tested in 384-well plates by using a distribution robot and cell viability was measured by Cell Titer Glow after 72 hours of cultivation. The obtained results are in Table 5 and are expressed as a percentage of the obtained result without any treatment.

TABLE 14

Comparative toxicity of statins on differentiated cells« MSC» SA01 derived from embryonic stem cells.

|  | Simvastatin | Lovostatin | Fluvostatin |
|---|---|---|---|
| Without Mevalonate | 48.7% | 53.6% | 32.8% |
| With Mevalonate | 98.3% | 96.4% | 104% |

The three tested statins have toxicity for these cells and in all the cases, the presence of mevalonate abolishes this toxicity. It should also be noted that fluvastatin is more toxic than simvastatin and that the latter is more toxic than lovostatin. These results are very similar to those obtained with the MPCs.

In order to experimentally validate the <<MSC>> cells derived from hES cells, we screened a bank of small molecules, the Prestwick bank. This bank consists of more than 1,200 molecules which represent the large majority of the products used in human clinical practice. The substances are used at the concentration of 2.5 µM. The cells are sown in 96-well or 384-well multiplates gelatinized beforehand in the presence or in the absence of mevalonate at the concentration of 2 mM. 24 hours later, the compounds of the bank are distributed by means of a robot of the Velocity type. The amount of ATP per well is determined from a Cell Titer Glow test 72 after adding the compounds from the bank. The screening criteria were the following:

A toxicity of more than 35% in the absence of mevalonate
A toxicity of less than 20% in the presence of mevalonate Three different screening tests were carried out. For the first screening, the MSC cells were derived from hES human cells SA01. The test was carried out in 28 multiwells with 96 wells in the presence of a culture medium containing 20% fetal calf serum. The average of the Z factors was 0.47. Under these conditions, 11 molecules over more than 1,200 tested were able to be isolated, including the three statins present in the bank (Lovostatin, Simvastatin, Fluvastatin).

The second screening was carried out by using MSC cells derived from another line of human embryonic stem cells, the line VUB01. In this test, the cells were sown in 384-well multiplates. The conditions of the screening were produced like the previous one. The average Z' factor was 0.55. The number of molecules sorted out in this way was 15 including the three statins present in the bank. A third screening was carried out on a 384-well plate with the same cells as those of the first screening. In this case, the Z' factor was 0.59. The number of molecules sorted out in this way was three including the three statins contained in the bank.

The obtained results in the three independent screenings are illustrated and summarized in the following table.

TABLE 15

| Cells | | Format | Z' Factor | Number of Hits | Statin |
|---|---|---|---|---|---|
| Screening 1 | « MSC» SA001 | 96 | 0.47 | 11 | 3 |
| Screening 2 | « MSC» VUB001 | 384 | 0.54 | 15 | 3 |
| Screening 3 | « MSC» SA001 | 384 | 0.59 | 3 | 3 |

The only molecules which we again found at each screening were the three statins contained in the bank. Therefore the conclusion may be drawn that the conditions of this bioassay using <<MSC>> cells derived from human embryonic stem cells, give the possibility of screening molecules inhibiting the synthesis of mevalonate in a sensitive and robust way. MSC cells derived from embryonic stem cells are excellent tools for high throughput screening. These properties are observed with all the MSCs derived from hES cells.

D) Conclusions

The differentiated cells of the MSC type derived from human embryonic stem cells have a sensitivity to statins of the same type as MPC cells and are robust, sensitive, specific tools and suitable for high throughput techniques for screening products having toxicity for muscle tissue and for inhibitors of the synthesis of mevalonate.

Example 4

Differentiated Cells of the MSC Type Derived from Human Induced Pluripotent Cells (iPS) as Tools for Predictive Toxicology of Muscle Tissue for High Throughput Screening Techniques Induced pluripotent cells iPS which share the essential characteristics of embryonic stem cells (self-renewal without any limitations and the possibility of differentiation into all the cell types making up an entire organism) are both easier to produce and pose less regulatory questions. These properties make these cells and their derivatives, good candidates for high throughput screening techniques.

A) Differentiated MSC Cells Derived from Human Induced Pluripotent Stem Cells: Tools for Predictive Toxicology in High Throughput Screening.

Development of high throughput screening technology requires the possibility of cultivating cells in multiwells without altering the biological functions and having automatable readout systems. The dosage of ATP should be able to determine the number of cells automatically.

In this test, the light emission is proportional to the amount of cell ATP. The preliminary experiments gave the possibility of verifying the relationship between the amount of ATP and the number of cells. In this type of test, the measured amount of ATP represents the number of cells.

Differentiated <<MSC>> cells derived from human induced pluripotent stem cells iPS were sown at a density of 2,000 cells per well among 384 wells and cultivated for 72 hours in the presence and in the absence of Simvastatin at the concentration of 2 µM. The different following culture conditions were tested:

Culture medium and ascorbic acid 2-phosphate
Culture medium and 1% of fetal calf serum
Culture medium and 10% of fetal calf serum
Culture medium and 20% of fetal calf serum The goal of the experiment was to both test the robustness of the test and to define the optimum conditions for conducting this test.

The results in figures are shown in the following table:

TABLE 16

| | Simvastatin | CV | DMSO | CV | Inhibition % | Z' Factor |
|---|---|---|---|---|---|---|
| AA2P | 235 856 | 5.6 | 631 378 | 3 | 63 | 0.76 |
| SVF 1% | 53 212 | 12.2 | 747 366 | 6 | 93 | 0.78 |
| SVF 10% | 294 847 | 14.6 | 1 343 308 | 6.3 | 78 | 0.63 |
| SVF 20% | 471 949 | 14.4 | 1 411 750 | 7 | 67 | 0.76 |

CV means coefficient of variation, being the standard deviation divided by the mean.
AA2P = Medium + 1 mM AA2P
SVF1% = Medium + 1% of fetal calf serum
SVF10% = Medium + 10% of fetal calf serum
SVF20% = Medium + 20% of fetal calf serum Under all the tested conditions, simvastatin has a large toxic effect on these cells, of more than 60%. This toxicity is very similar to the one observed with muscle precursor cells (MPCs). It should also be noted that under all the experimental conditions, the Z' factor which is the statistical indicator of the size effect is greater than 0.60 which indicates that these tests may be used for high throughput screenings. On the other hand, it is possible to practice this type of test in a synthetic medium without any presence of animal serum. In this case, the observed toxicity is 63% with a Z' factor of 0.76. The optimum culture conditions for this test are the medium in the presence of 1% of fetal calf serum. Under these conditions, the reduced number of cells is 93% with a Z' Factor of 0.78.

In order to experimentally validate the <<MSC>> cells derived from iPS cells, we screened a bank of small molecules, the Prestwick bank. This bank consists of more than 1,200 molecules which represent the large majority of products used in human clinical practice. The substances are used at the concentration of 2.5 µM. A schematic illustration of the procedure is shown in Annex 1. The cells are sown in 96-well or 384-well multi-plates gelatinized beforehand in the presence and in the absence of mevalonate at the concentration of 2 mM. 24 hours later, the compounds of the bank are distributed by means of a robot of the Velocity type. The amount of ATP per well is determined by means of a Cell Titer Glow test 72 after adding the compounds of the bank. The screening criteria were the following:

Toxicity of more than 80% in the absence of mevalonate
Toxicity of less than 50% in the presence of mevalonate The screening test was carried out by using <<MSC>> cells derived from iPS cells. 2,000 cells were sown in 16 plates of 384 wells in the presence and in the absence of mevalonate. 24 hours later, the cells were put into contact with the molecules from the Prestwick bank. The measurement was conducted after 72 hours of cultivation. The Z' factor of this test is greater than 0.70.

With these criteria, we only identify three molecules which are the only three statins contained in the bank. These data show that it is possible to use MSC cells derived from iPS cells for high throughput screenings. The latter cells have functional characteristics very similar to MSC cells derived from embryonic stem cells.

B) Conclusions

The differentiated MSC cells derived from human induced pluripotent cells have a sensitivity to statins of the same type as the MPC cells and are cell tools suitable for high throughput screening techniques for products having toxicity for muscle tissue. With this type of cells, the cell test developed for high throughput screening is both robust and sensitive. It should be added that it is possible to conduct this test under conditions of a synthetic and defined medium.

Example 5

High Throughput Screening and Metabolism of Mevalonate: Applications for Muscle Atrophy and for Cancer A) Introduction In this series of tests, the goal is to isolate molecules which may modify the toxic effect of inhibitors of HMG CoA reductase. In this way, it will therefore be possible to sort out the molecules on the capability of reducing or specifically enhancing the toxic effects of inhibitors of HMG CoA reductase.

The molecules which reduce the toxic effect may be associated with inhibitors of HMG CoA reductase in order to reduce the deleterious effects of the latter on muscle tissue. On the other hand, these molecules may have more extensive applications in the protection of muscle atrophy. Indeed, it was shown that in the large majority of muscle atrophies, the atrigon protein is increased and this regardless of the origin of muscle atrophy. Further, the treatment of the cells by inhibitors of HMG CoA reductase increases the synthesis of the atrogin. It is therefore legitimate to believe that the cells treated by inhibitors of HMG CoA reductase may form an in vitro cell model of muscle atrophy. Muscle atrophy is an extremely common pathology which is associated with many pathologies (neuromuscular diseases, cancer or HIV). In the latter pathologies, atrophy is a poor prognosis factor. Preventing or reducing muscle atrophy is therefore a significant therapeutic goal.

The molecules enhancing the toxic effect are of interest for more than one reason. Knowing these molecules might give the possibility of avoiding their therapeutic combinations with inhibitors of HMG CoA reductase in order to prevent potential toxic effects. On the other hand, the inhibitors of HMG CoA reductase are used in combination with anticancer molecules for increasing their therapeutic potentials in anti-tumoral treatment. The definition of the molecules enhancing the effects of inhibitors of HMG CoA reductase should give the possibility of proposing a rational basis for defining therapeutic combinations for treatments of tumoral diseases.

B) Principles for the Screening of the Bank of Small Molecules with Differentiated MSC Cells Derived from Pluripotent Cells Treated with Inhibitors of HMG COA Reductase MSC cells derived from pluripotent cells are sown in the presence of an inhibitor of HMG CoA reductase and treated with the bank of small molecules. In this experiment, the inhibitor of HMG CoA reductase used was simvastatin at a concentration of 2 µM. After 72 hours of cultivation, the number of cells is determined for each well by the Cell Titer Glow technique. In order to demonstrate the feasibility of the technique, the Prestwick bank of small molecules was selected, which contains more than 1,200 compounds, for which the large majority of active ingredients are used in human clinical practice like for Example 2. The working process is schematized in Annex 2.

C) Results of the Screening on Differentiated MSC Cells Derived from Human Pluripotent Cells Treated with Simvastatin.

The screening conditions were:
2,000 cells per well among 384 wells
D+1 treatment with compounds from the Prestwick bank
D+1 treatment with simvastatin
D+4 read out of the results with Cell Titer Glow.

With the screening, it is possible to identify two types of compounds. The first has a protective role and limits the toxicity of inhibitors of HMG CoA reductase for MSC cells. The second exacerbate toxicity of the statins.

The selections of the thresholds was carried out by calculating the average of the samples and the standard deviation. With this methodology, a series of protective compounds and a series of compounds exacerbating toxicity of simvastatin were determined.

For the first compounds, the following results were obtained which are shown in Table 14.

TABLE 17

| NUMBER OF COMPOUNDS HAVING LARGER AVERAGES | | | | | | |
|---|---|---|---|---|---|---|
| M + 1ET | M + 2ET | M + 2.5ET | M + 3ET | M + 4ET | M + 5ET | M + 6ET |
| Number of hits 105 | 11 | 4 | 3 | 2 | 1 | 0 |

M = Average of the samples
ET = standard deviation
Number of hits = number of molecules having an average above the average + N standard deviations 11 compounds have a larger average than that with two standard deviations and only 2 compounds have a larger average than that with 4 standard deviations. The thereby selected compounds belong to different drug classes (antihypertensives, antihistaminics, andtidepressors or anticholinergics). By using this approach, it was therefore possible to isolate compounds which allow reduction in the toxic effect of statins. One of the first applications of the thereby isolated molecules will be to prevent the deleterious effects of statins and thereby extend their clinical indications. On the other hand, these molecules may have a protective role in muscle atrophy, a very common pathology for which therapeutic tools are still too reduced. Indeed, MSC cells treated with inhibitors of the synthesis of mevalonate represent a model in the culture dish for muscle atrophy observed in many primitive pathologies (muscle dystrophy) or secondary pathologies (sarcopenia, cancers, HIV, ageing). This type of screening will allow definition of drug strategies for reducing muscle atrophy.

For the second series of compounds which enhance the effect of statins, the following results were obtained which are shown in Table 15.

TABLE 18

| Number of compounds having lower averages | | | | | |
|---|---|---|---|---|---|
| M − 1ET | M − 2ET | M − 3ET | M − 4ET | M − 5ET | M − 6ET |
| Number of hits 650 | 203 | 59 | 42 | 32 | 27 |

M = Average of the samples
ET = Standard deviation
Number of hit = number of molecules having an average of less than the average + N standard deviations 32 compounds have a lower average by 5 standard deviations. Among these 32 compounds, unexpectedly three statins present in the bank are found. Indeed, the selected concentration of simvastatin is sub-optimum and under these conditions, it is expected that the statins present in the bank will be detected. For finer analysis, it is possible to isolate compounds for which toxicity is enhanced in the presence of simvastatin. Indeed among the 32 compounds, 5 compounds were not revealed in toxicity tests in the absence of simvastatin. It is therefore possible to isolate compounds which specifically increase the observed toxicity in the presence of a statin. Among these molecules, anti-tumoral molecules and molecules which have recognized muscular toxicity are found. With this test, it is possible to predict the molecules which enhance the tissue toxicity due to statins. With this approach, it is possible to prevent toxicities due to drug interactions in the presence of statins. This simple functional test to be set into place may therefore be practiced systematically for all novel molecules before their passing into clinical practice.

The screening strategy is the following. The first screening allows isolation of the molecules which enhance toxicity in the presence of cells treated with statins. Counter-screening is then performed on the thereby isolated molecules from the first screening in order to remove the molecules which have toxicity in the absence of statins. In this way, the specificity of the toxicity in the presence of statins is ensured. It is significant that, with this strategy among the 5 sorted out molecules, 3 are antitumoral molecules.

C) Conclusions

The developed cell test (bioassay) which uses as a cell source, differentiated MSC cells derived from pluripotent cells treated with an inhibitor of HMG Coa reductase, Simvastatin, allows sorting out of the molecules which protect from the toxic effect of simvastatin and of the molecules which exacerbate this effect.

The first families of molecules may have therapeutic applications for limiting the toxic effects of inhibitors of HMG Coa reductase and for preventing muscle atrophy, a major pathology.

The second families of molecules may have toxicological applications for predicting undesirable drug interactions and therapeutic applications in tumoral treatment for determining the molecule families which may be combined with inhibitors of HMG Coa reductase for obtaining cytotoxic effects on tumoral cells and on <<tumoral stem>> cells.

The invention claimed is:

1. A method for selecting pharmaceutical compounds enhancing effects of inhibition of synthesis of mevalonate wherein the selected compounds can enhance cell toxicity in the presence of inhibitors of the synthesis of mevalonate comprising a step for contacting the cells with the pharmaceutical compounds to be tested, wherein the cells are obtained by a method for producing cells of the MSC type from human pluripotent cells or from induced stem cells comprising cultivating human pluripotent cells or induced stem cells in a culture medium comprising a) one or more growth factors selected from FGFs, HGF, PDGFs, EGF, herugulins and VEGFs, and b) one or more antioxidants selected from ascorbic acid and its derivatives, vitamin E and N-acetylcysteine.

2. A method for selecting pharmaceutical compounds according to claim 1, wherein the cells of the MSC type obtained from induced stem cells are cultivated in the presence of 1% of fetal calf serum.

3. A method for selecting pharmaceutical compounds according to claim 1, wherein the cells are contacted with an inhibitor of HMG CoA reductase, and other reductases, or simvastatin.

4. A method for selecting pharmaceutical compounds according to claim 1, comprising a first screening that allows isolation of the molecules which enhance toxicity in the presence of cells treated with statins and then a counter-screening is performed on the thereby isolated molecules from the first screening in order to remove the molecules which have toxicity in the absence of statins.

* * * * *